United States Patent [19]

Franco et al.

[11] Patent Number: 5,271,935
[45] Date of Patent: Dec. 21, 1993

[54] ANTIBIOTIC, CAMMUNOCIN, A PROCESS FOR THE PREPARATION THEREOF, AND THE USE THEREOF AS A PHARMACEUTICAL

[75] Inventors: Christopher M. M. Franco; Sugata Chatterjee; Erra K. S. Vijayakumar; Bimal N. Ganguli, all of Bombay, India; Richard H. Rupp, Königstein/Taunus, Fed. Rep. of Germany

[73] Assignee: Hoechst Aktiengesellschaft, Frankfurt am Main, Fed. Rep. of Germany

[21] Appl. No.: 850,162

[22] Filed: Mar. 13, 1992

Related U.S. Application Data

[63] Continuation of Ser. No. 305,270, Feb. 2, 1989, abandoned.

[30] Foreign Application Priority Data

Feb. 5, 1988 [DE] Fed. Rep. of Germany ....... 3803383

[51] Int. Cl.⁵ .............................................. A61K 35/74
[52] U.S. Cl. ............................... 424/115; 530/300; 514/2
[58] Field of Search ................... 530/300; 514/2; 424/115; 435/71.3

[56] References Cited

U.S. PATENT DOCUMENTS

| | | |
|---|---|---|
| 2,686,753 | 8/1954 | Colingsworth ............... 424/115 |
| 3,644,617 | 5/1968 | Axelrod et al. ............... 424/115 |
| 4,331,594 | 5/1982 | Hamill et al. ................ 424/115 |
| 4,524,135 | 6/1985 | Abbott et al. ................. 435/69 |
| 4,537,770 | 8/1985 | Michel et al. ................ 424/118 |
| 4,703,033 | 10/1987 | Seebach ....................... 514/11 |
| 4,931,352 | 6/1990 | Fromtling et al. ........... 435/71.3 |

OTHER PUBLICATIONS

Eliopoulus et al. 1986. Antimicrobiol Agents and Chemotherapy, Oct. pp. 532-535.
CRC Handbook of Antibiotic Compounds, vol. IV, Part 1, pp. 313-321, Janos Berdy (author), CRC Press, Boca Raton, Florida (1980).
Debono et al., J. Antibiotics 40:761-777 (1987).

*Primary Examiner*—Robert A. Wax
*Assistant Examiner*—Keith C. Furman
*Attorney, Agent, or Firm*—Finnegan, Henderson, Farabow, Garrett & Dunner

[57] ABSTRACT

Cammunocin, an active substance which can be obtained by cultivation of Streptomyces species Y-84,36210 (DSM 4329), has antibiotic and immunosuppressant activity.

6 Claims, 4 Drawing Sheets

# ANTIBIOTIC, CAMMUNOCIN, A PROCESS FOR THE PREPARATION THEREOF, AND THE USE THEREOF AS A PHARMACEUTICAL This application is a continuation of application Ser. No. 07/305,270 filed Feb. 2, 1989, now abandoned.

BACKGROUND OF THE INVENTION

FIELD OF THE INVENTION

The present invention relates to a new antibiotic, which is called cammunocin, to a process for the preparation thereof from Streptomyces species Y-84,36210 (deposited at the Deutsche Sammlung für Mikroorganismen (German Microorganism Collection) on Dec. 23, 1987, under the No. DSM 4329), to the variants and mutants thereof, and to the use of cammunocin as a pharmaceutical.

Str. sp. Y-84,36210 was isolated from a soil sample collected at Poona, Maharashtra, India. Variants and mutants of the culture No. HIL Y-84,36210 can be obtained in a known manner by use of a mutagen such as, for example, N-methyl-N'-nitro-N-nitrosoguanidine or ultraviolet light. The microorganism Str. sp. Y-84,36210 belongs to the order of Actinomycetales, family Streptomycetaceae and genus Streptomyces.

Str. sp. Y-84,36210 is regarded as a new strain because it differs in some of its morphological, cultural and physiological properties from the known strains, as is evident from the description which follows. Another reason for regarding it as a new strain is that it produces a new antibiotic complex whose characteristics are given in the following description, which is called cammunocin herein, and to which the present invention relates.

SUMMARY OF THE INVENTION

Figure 1:
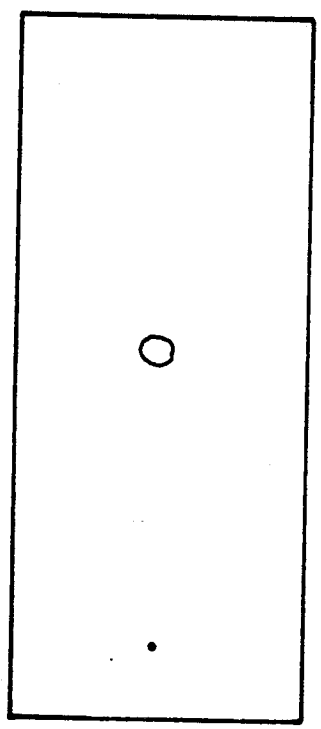
FIG. 1 shows a thin layer chromatogram (TLC) using the mobile phase EtOAc:MeOH:H$_2$O (4:4:1).

As is evident from the following detailed description of the invention, cammunocin of this invention is a peptide antibiotic but differs from all known peptide antibiotics such as actinomycin, viridogrisein, valinomycin, chinomycin, cyclosporin, polymyxin or amphomycin. In contrast to the other known peptide or peptide-containing antibiotics, cammunocin requires at least about 10 mM calcium ions in order to display an antibacterial effect. This differs distinctly from other known antibiotics such as amphomycin, glumamycin, zaomycin and the A 21978 C complex, whose requirements for calcium ions are lower, at 1.0 mM, in order to show an antibiotic effect. Amphomycin, glumamycin and zaomycin belong to the class of cyclic lipopeptide antibiotics mentioned in the CRC Handbook of antibiotic compounds, Volume IV, Part 1, pages 313–327, Janos Berdy (author), CRC Press, Boca Raton, Florida (1980). An A 21978 C complex, likewise a cyclic lipopeptide antibiotic, is described in J. Antibiotics 40, 761–777 (1987).

This invention additionally relates to a process for the preparation of the new antibiotic complex cammunocin, which comprises culturing Str. sp. Y-84,36210, the variants and mutants thereof, under aerobic conditions at a temperature which is preferably between about 18° and 370° C. in an aqueous nutrient medium which contains sources of carbon and of nitrogen, and minerals, at a pH which is preferably between about 6 and 9, and obtaining the antibiotic complex from the nutrient medium.

The new antibiotic of this invention is active in vitro against a number of Gram-positive microorganisms, but only in the presence of calcium ions. It is likewise active as an immunomodulating substance and can, accordingly, be used in human medicine.

The present invention furthermore relates to a process for the isolation of Str. sp. Y-84,36210 from soil, entailing use, in a known manner, of a nutrient solution which preferably has a pH between about 6.5 and 8.5.

DESCRIPTION OF THE PREFERRED EMBODIMENT

The nutrient solution used for the isolation of the microorganisms from soil is composed of sources of carbon and of nitrogen, and inorganic nutrient salts and solidifying agents. An example of a preferred source of carbon is glucose, starch, dextrin, glycerol, sucrose or molasses.

Preferred sources of nitrogen are peptone, yeast extract, beef extract, malt extract, casein or amino acids such as arginine or asparagine. An example of a solidifying agent which can be used is agar. Suitable and preferred inorganic nutrient salts are sodium, potassium, magnesium or calcium salts of phosphoric or sulfuric acid.

A microorganism according to the invention projects colorless aerial mycelia from branched substrate mycelia. Spiral chains of spores are formed on the aerial mycelia. The spirals are open. Short chains of spores representing the RA section are likewise common. Formation of neither whorls nor ascospores is observed. Mature chains of spores have 30–50 spores per chain. The properties of the microorganism when cultured on various agar media is described as follows (cf. The Oxoid Manual 1972, 2nd edition, published by Oxoid limited, london, GB or Difco Manual, 9th edition 1977, published by Difco Laboratories, Detroit, Mich., USA):

1. Yeast extract/malt extract agar
   Growth: good, furrowed, dry
   Aerial mycelium: good, powdery, pate bluish gray
   Underside: black/purple
   Soluble pigment: brown/purple
2. Oatmeal agar
   Growth: copious, fiat, dry
   Aerial mycelium: copious, powdery, pate gray
   Underside: dark brown/purple
   Soluble pigment: brown/purple
3. Inorganic salts/starch agar
   Growth: copious, raised, dry
   Aerial mycelium: good, powdery, pate bluish gray
   Underside: dark blackish violet
   Soluble pigment: pale mauve
4. Glycerol/asparagine agar
   Growth: good, raised, dry
   Aerial mycelium: good, powdery, grayish pink
   Underside: black/purple
   Soluble pigment: pate purplish brown
5. Peptone/yeast extract/iron agar
   Growth: good, furrowed, moist Aerial mycelium: none
Underside: pate yellow
Soluble pigment: pate brown 6. Tyrosine agar
   Growth: copious, furrowed, dry
   Aerial mycelium: copious, powdery, pate grayish blue
   Underside: dark blackish violet
   Soluble pigment: pate brownish violet 7. Sucrose/nitrate agar
   Growth: copious, fiat, dry
   Aerial mycelium: good, powdery, pate bluish gray
   Underside: pate yellow
   Soluble pigment: pate violet 8. Peptone/beef extract agar (nutrient agar)
   Growth: moderate, raised, dry
   Aerial mycelium: weak, powdery, dark gray
   Underside: grayish pink
   Soluble pigment: -

The soluble pigment is a pH indicator: it becomes pinkish red in acid medium and bluish violet in the alkaline range.

The optimal temperature range for growth of the microorganism according to the invention is between about 25° and 35° C. The microorganism liquifies gelatin in glucose/peptone/gelatin medium, hydrolyzes starch in inorganic salt/starch agar and coagulates skim milk.

Str. sp. Y-84,36210 grows well on Czapek's agar solution (cf. Oxoid Manual).

A very sparse formation of dark pigment is observed only in tyrosine agar, there being no pigment formation in peptone, yeast extract, iron agar or tryptone/yeast extract broth.

The assimilation scheme of this microorganism for sources of carbon is as follows (in Pridham-Gottlieb medium):

Positive: D-glucose, L-arabinose, D-xylose, I-inositol, D-mannitol, D-fructose, rhamnose, galactose, maltose, cellobiose, sodium glutamate, mannose, lactose
Doubtful: sucrose, salicin
Negative: raffinose, cellulose, dulcitol Str. sp. Y-84,36210 is inhibited by streptomycin in concentrations above 1.6 $\mu$g/ml, tolerates NACl concentrations of about 7-10% and has a pH tolerance range of about 5.5-9.0.

The published data on the cultural and physiological properties of known microorganisms show distinct differences from the microorganism according to the invention.

Furthermore, Str. sp. Y-84,36210 produces, when it is fermented, the new antibiotic complex cammunocin.

Based on the abovementioned observations, the microorganism according to the invention can be regarded as a new Streptomyces species.

It is self-evident to those skilled in the art that this invention is not confined to the specific organism defined above but includes all those spontaneous and artificial mutants and variants which are derived from said microorganism and which have the ability to form the new antibiotic complex cammunocin.

The present invention furthermore relates to a process for the preparation of cammunocin, which comprises culturing Str. sp. Y-84,36210 by fermentation, preferably at a pH between about 6.0 and 9.0, and preferably at a temperature of between about 18° and 37° C., under aerobic conditions in a nutrient medium which contains sources of carbon and of nitrogen, and inorganic nutrient salts and trace elements, and isolating the compounds from the culture broth in a known manner, as described herein.

Examples of suitable and preferred sources of carbon for the nutrient medium used for the preparation of the new antibiotic are glucose, starch, dextrin, glycerol, sucrose, molasses or oil. Suitable and preferred sources of nitrogen in the nutrient medium for the preparation of the new antibiotics are soybean meat, yeast extract, beef extract, malt extract, corn steep liquor, peptone or casein. Suitable inorganic nutrient salts/mineral salts for use in the nutrient medium for the preparation of the new antibiotics are preferably sodium chloride, magnesium sulfate, ammonium sulfate or calcium carbonate. Trace elements which are preferably used are iron, manganese, copper, zinc or cobalt.

In a preferred embodiment of the present invention, Str. sp. Y-84,36210 is cultured at about 26°-28° C. and pH about 6.4-6.6. The highest yields of the compounds are obtained after fermentation has lasted about 40-45 hours. The fermentation preferably takes the form of a submerged fermentation. The course of the fermentation and the formation of the new antibiotic complex can be followed by use of the antibacterial activity of the culture liquid and of the mycelium against *Staphylococcus aureus* 209 P in agar medium containing 30 mM calcium chloride.

It is possible, where appropriate, to add to the nutrient medium during the fermentation of the culture an antifoam agent such as, for example, DESNIOPHEN (Polyols from Bayer AG, Leverkusen).

Cammunocin can be obtained from the culture broth, for example by direct adsorption on suitable adsorbents or by solvent extraction followed by adsorption. Examples of preferred solvents are mixtures of ethyl acetate or chloroform with n-propanol; particularly preferred is an ethyl acetate/n-propanol mixture (2:1). For example, it is possible for the culture filtrate, or the solvent extract of the culture filtrate containing the compound according to the invention, to be adsorbed on active charcoal, polymeric adsorbents such as, for example, DIAION HP-20 (Mitsubishi Chemical Industries, Japan) or AMBERLITE XAD (polymeric adsorbent composed of a matrix of polystyrene, acrylate or amine oxide with a mean pore diameter of $40-225 \times 10^{-10}$ m, Rohm & Haas Co., USA). The solvent extract is preferably concentrated to remove the solvent, and then chromatographed on the adsorbent. The compound according to the invention can be eluted from the adsorbents using suitable mobile phases such as, for example, chloroform, methanol or acetone, or using mixtures of these solvents with one another or with water, and the eluates can then be evaporated to dryness. The eluent which is preferably used is methanol.

Cammunocin can also be isolated from the culture filtrate by use of ion exchange chromatography. Examples of suitable resins are anion exchange resins of the weakly basic polystyrene, polyamine or crosslinked amino alcohol polyacrylate type, such as, for example DOWEX (Dow Chemical Company, USA) or AMERLITE IRA 68 (Rohm & Haas Co., USA). The ion exchanger which is preferably used is AMBERLITE IRA 68 (acrylic type, tertiary amine functionality). In this process the culture filtrate is preferably subjected to a column chromatography, using the anion exchange resin AMBERLITE IRA 68 (Cl$^-$).

The compound according to the invention is initially adsorbed by the ion exchanger and is then eluted using suitable mobile phases such as, for example, aqueous or methanolic sodium or potassium chloride solutions, or dilute hydrochloric acid or sodium hydroxide solutions, with a 2M NACl solution preferably being used. The active eluates can be combined and the salts can be removed using the abovementioned adsorption chromatography. The active eluates from which the salts have been removed and which have been obtained in this way are collected and concentrated.

The abovementioned concentrated cammunocin-containing eluates can be further purified in a variety of ways. For example, readsorption and elution using active charcoal, polymeric adsorbents such as, for example, AMBERLITE XAD-4 (composed of a polystyrene matrix, mean pore diameter $40 \times 10^{-10}$ m) and 7 (composed of an acrylate matrix, mean pore diameter $90 \times 10^{-10}$ m, Rohm & Haas Co., USA), DIAION HP-20 (Mitsubishi Chemical Industries, Japan), gel filtration with lipophilic gel filtration material such as, for example, SEPHADEX LH-20 and G-series gels (Pharmacia Fine Chemicals AB, Sweden) and equivalent products, as well as ion exchange gel filtration with gels having the diethylaminoethyl (DEAE) functionality such as, for example, Sephadex ® DEAE gels (Pharmacia Fine Chemicals AB, Sweden), and adsorption chromatography on alumina and silica gel, can be satisfactorily combined together for the further purification. In addition, it is also possible to use thin-layer chromatography, medium-pressure and high-pressure liquid chromatography with suitable adsorbents such as silica gel and modified silica gel $C_{18}$ (obtainable, for example, by reaction of silica gel with octadecyltrichlorosilane) and suitable eluents. Said purpose can furthermore be satisfactorily achieved by countercurrent chromatography using a defined solvent system.

Cammunocin is a colorless amorphous powder which is soluble in water, methanol, ethanol, propylene glycol and dimethyl sulfoxide. It is sparingly soluble or insoluble in acetone, methylene chloride, ethyl acetate, chloroform, hexane and petroleum ether (40°-60°). It shows a negative reaction in the ninhydrin color test.

The Rf values for cammunocin in the thin-layer chromatography (TLC) systems indicated below are as follows:

TLC plate: precoated silica gel plate, Article No. 5554 from E. Merck, Darmstadt.

|  | EtOAc:MeOH:H$_2$O 4:4:1 | Butanol:AcOH:H$_2$O 4:4:1 |
|---|---|---|
| Cammunocin Rf | 0.47 | 0.39 |

FIG. 1 shows the TLC using the mobile phase: EtOAc:MeOH: H$_2$O (4:4:1). Detection at 254 nm.

Figure 2:
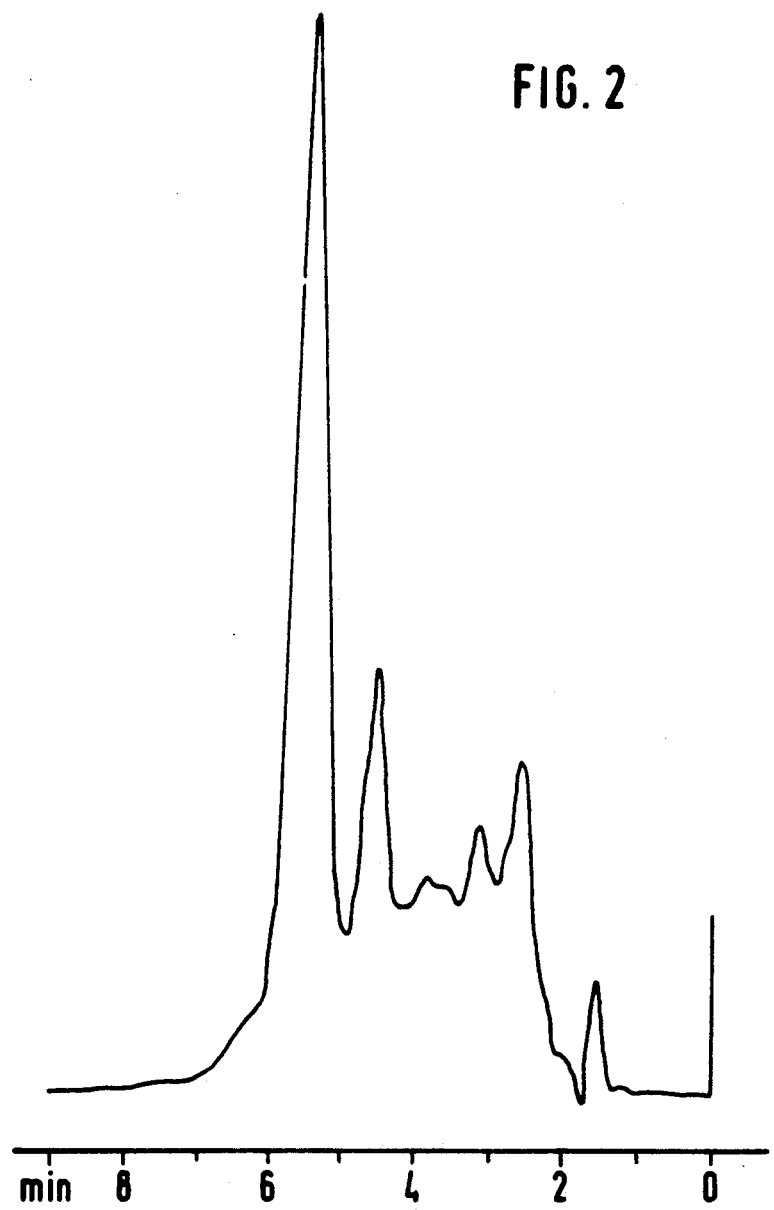
FIG. 2 shows an analytical high-pressure liquid chromatogram (HPLC).

FIG. 2 shows the analytical high-pressure liquid chromatography (HPLC). The HPLC was carried out as follows:

Column packing: ODS-HYPERSIL (10 μ, 4×120 mm) (HPLC material with octadecyltrichlorosilane groups from Shandon, USA)

Flow rate: 0.5 ml/minute

Detection: at 234 nm

Solvent: MeOH: 1% strength aqueous acetic acid (55:45)

Cammunocin melts at 270° C. with decomposition.

Figure 3:
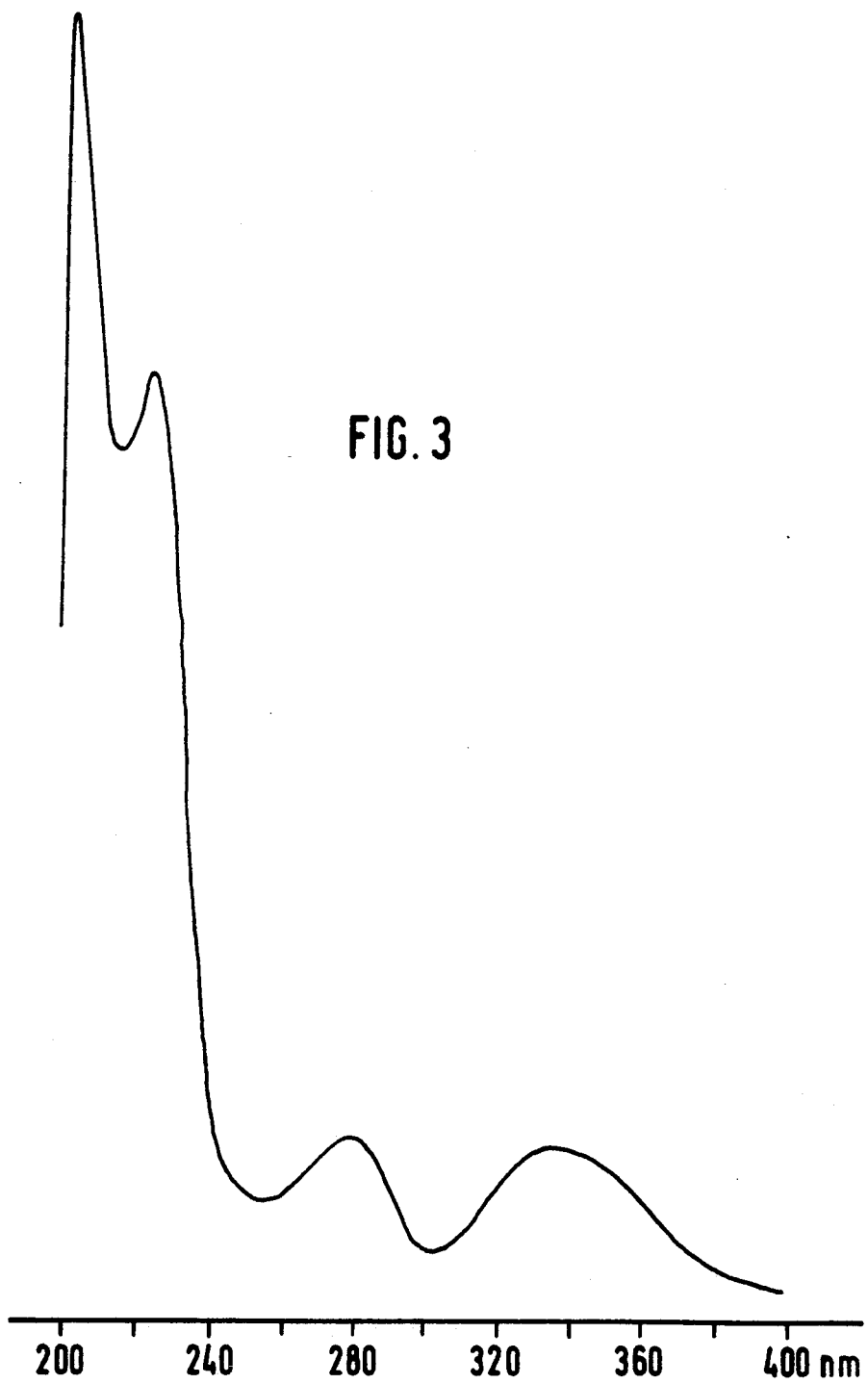
FIG. 3 shows the UV max in methanol at about 224, 280 and 345 nm.

The spectroscopic data for cammunocin are listed hereinafter:

1. UV max in methanol at about 224, 280 and 345 nm—see FIG. 3. The UV absorption maxima of cammunocin were determined at a concentration of 0.2 g per liter. The absorption spectrum was recorded in the range 200 to 800 nm using a Uvicon 810 spectrophotometer.
2. The IR spectrum (KBr disk) was recorded using a Perkin Elmer P.E. 521 spectrometer—see FIG. 4.

The abovementioned spectroscopic data, and the chemical and spectroscopic analyses described in Example VI indicate that cammunocin is a complex of related peptide antibiotics.

A unique characteristic of cammunocin is that it displays its antibiotic effect against Gram-positive bacteria only in the presence of calcium ions. Other metal ions, such as, for example, sodium, potassium, barium, rubidium and magnesium, do not have the same effect. This is why cammunocin is tested in an agar medium which contains at least about 10 mM calcium chloride.

Cammunocin in vitro in the abovementioned agar enriched with calcium shows an effect against sensitive and resistant *Staphylococcus aureus* and *Streptomyces faecalis* strains and against *Bacillus subtilis, Sarcina lutea, Streptococcus pyogenes* and *Micrococcus luteus*. The minimum inhibitory concentration (MIC) of cammunocin for various microorganisms has been determined. The results are listed in Table 1 which follows:

TABLE 1

MIC of cammunocin
Test medium: Müller-Hinton agar (cf. Oxoid Manual) with the addition of various Ca$^{2+}$ concentrations.

| Test organism | Ca$^{2+}$ concentrations | | | | |
|---|---|---|---|---|---|
|  | 0.0 mM | 2.5 mM | 10.0 mM | 30.0 mM | 60.0 mM |
| S.aureus 209 P | >100.0 | 25.0 | 6.3 | 1.6 | <0.1 |
| S.aureus 20464 Mac(R) | >100.0 | 100.0 | 25.0 | 1.6 | 1.6 |
| S.aureus 3066 Met(R) | >100.0 | 50.0 | 6.3 | 6.3 | 0.8 |
| S.aureus R 85, Em(R) | >100.0 | >100.0 | >50.0 | 25.0 | 6.3 |
| S.aureus R 85/M, Em(R) | >100.0 | >100.0 | >50.0 | 2.5 | 1.6 |
| S.aureus 712 Met(R) | >100.0 | 100.0 | 6.3 | 6.3 | 0.4 |
| S.aureus 789 Met(R) | >100.0 | 100.0 | 6.3 | 1.6 | 0.8 |
| Str.faecalis UD86 | >100.0 | 100.0 | 25.0 | 6.3 | 0.8 |
| Str.faecalis Eder Mac(R) | >100.0 | 100.0 | 25.0 | 6.3 | 1.6 |
| S.aureus MLS 11 | >100.0 | >100.0 | 12.5 | 3.2 | 1.6 |
| S.aureus MLS 14 | >100.0 | 50.0 | 25.0 | 12.5 | 1.6 |
| S.aureus MLS 16 | >100.0 | 100.0 | 25.0 | 25.0 | 1.6 |
| S.aureus 011UC5 | >100.0 | 100.0 | >50.0 | 12.5 | 1.6 |
| S.aureus 011GR5 | >100.0 | 100.0 | >50.0 | >50.0 | NT |
| Str.faecalis 02 | >100.0 | 100.0 | 25.0 | 6.3 | 1.6 |

TABLE 1-continued

MIC of cammunocin
Test medium: Müller-Hinton agar (cf. Oxoid Manual) with
the addition of various $Ca^{2+}$ concentrations.

| Test organism | $Ca^{2+}$ concentrations | | | | |
|---|---|---|---|---|---|
| | 0.0 mM | 2.5 mM | 10.0 mM | 30.0 mM | 60.0 mM |
| *Micrococcus luteus* | >100.0 | 3.2 | 0.8 | 0.2 | <0.1 |
| *Sarcina lutea* | >100.0 | 25.0 | 6.3 | 1.6 | 0.8 |
| *Bacillus subtilis* | >100.0 | 100.0 | 6.3 | 3.2 | 0.8 |
| *E. coli* 9632 | >100.0 | >100.0 | >100.0 | >100.0 | >100.0 |
| *E. coli* 2231 | >100.0 | >100.0 | >100.0 | >100.0 | >100.0 |
| *Candida albicans* | >100.0 | >100.0 | >100.0 | >100.0 | >100.0 |
| *Aspergillus niger* | >100.0 | >100.0 | >100.0 | >100.0 | >100.0 |

$Mac^{(R)}$ = resistant to macrolide antibiotics
$Met^{(R)}$ = resistant to methicillin.
$Em^{(R)}$ = resistant to erythromycin

IMMUNOMODULATING EFFECT

The immunomodulating effect of cammunocin was tested as follows:

Hemolysis plaque test (PFC):

Female Swiss mice weighing 16–18 g (6 per group) are sensitized by intraperitoneal injection of sheep erythrocytes ($5 \times 10^8$ cells). After 5 days, the mice are sacrificed by cervical dislocation, and the spleen is removed and stored in ice-cold Dulbecco's solution. The splenocytes are obtained by cautiously breaking up the spleen on a fine-mesh wire grid. Their viability is determined, and the amount thereof is adjusted to about $6 \times 10^6$ cells/ml. The splenocytes are then reacted with sheep erythrocytes in the presence of complement in a Cunningham chamber at 37° C. under 5% $CO_2$. The plaques which have formed are counted after 2 hours.

Cammunocin was injected intraperitoneally or subcutaneously, in doses of 5, 10 and 20 mg/kg, or of 10 mg/kg each day from the day of sensitization onwards. The last dose of the compound was administered on day 5, one hour before the animals were sacrificed. The results are listed in Table 2.

TABLE 2

| Dose mg/kg. × 5 | Administration route | Percentage inhibition of PFC |
|---|---|---|
| 5.0 | i.p. | 31.20 |
| 10.0 | i.p. | 40.66 ± 4.67 |
| 20.0 | i.p. | 41.4 ± 4.89 |
| 10.0 | s.c. | 38.4 |

These results show that cammunocin has an immunosuppressant effect and thus can be used as an immunosuppressant, for example in transplantations.

The pharmacological properties qualify the compounds according to the invention for use as a therapeutic agent. Accordingly, the invention also relates to pharmaceuticals containing cammunocin in addition to customary and generally known auxiliaries and/or vehicles, as well as to the use of cammunocin for the preparation of pharmaceuticals having an antibiotic and/or immunosuppressant effect in a manner known per se.

The invention is to be explained in detail hereinafter on the basis of some preferred examples, but it should not be regarded as confined to these examples.

EXAMPLE 1

Isolation of Streptomyces sp. Y-84,36210 from Soil (a) Preparation of the isolation nutrient media

| Medium 1: | Glucose | 1.0 g |
|---|---|---|
| | Glycerol | 1.0 g |
| | L-arginine | 0.3 g |
| | $K_2HPO_4$ | 0.3 g |
| | $MgSO_4.7H_2O$ | 0.2 g |
| | NaCl | 0.3 g |
| | Yeast extract | 0.2 g |
| | $Fe_2(SO_4)_3$ | 10.0 mg |
| | $CuSO_4.5H_2O$ | 1 mg |
| | $ZnSO_4.7H_2O$ | 1 mg |
| | $MnSO_4.7H_2O$ | 1 mg |
| | Agar | 15.0 g |
| | Distilled water | 1 l |
| | pH | 6.5 |
| Medium 2: | Glucose | 2.0 g |
| | L-asparagine | 1.0 g |
| | $K_2HPO_4$ | 0.5 g |
| | $MgSO_4.7H_2O$ | 0.5 g |
| | Soil extract | 200 ml |
| | Agar | 15.0 g |
| | Distilled water | 800 ml |
| | pH | 8.0 |
| Medium 3: | Starch | 10.0 g |
| | Casein | 0.3 g |
| | $KNO_3$ | 2.0 g |
| | NaCl | 2.0 g |
| | $K_2HPO_4$ | 2.0 g |
| | $MgSO_4.7H_2O$ | 0.05 g |
| | $CaCO_3$ | 0.02 g |
| | $FeSO_4$ | 0.01 g |
| | Agar | 15.0 g |
| | Distilled water | 1 l |
| | pH | 7.2–7.5 |

The media are sterilized at 121° C. for 30 minutes. On each occasion, the sterilized media are allowed to cool to 45° C., introduced into Petri dishes and left to solidify.

(b) Preparation of the Soil Suspension 1 g of soil is heated in a hot-air oven at 110° C. for 1 hour. After the soil has cooled it is suspended in distilled water and thoroughly shaken. The soil is allowed to settle, and the supernatant is used to inoculate each one of the abovementioned isolation nutrient media.

(c) Inoculation of the Isolation Medium 1 ml of the soil suspension is transferred into Petri dishes which each contain 50 ml of any one of the abovementioned isolation media.

(d) Isolation of Streptomyces sp. Y-84,36210

The inoculated Petri dishes are incubated at 37° C. for 10 days, and Streptomyces sp. Y-84,36210 is isolated from the growing microorganisms.

EXAMPLE 2

Culturing of Streptomyces sp. Y-84,36210 for the Preparation of Cammunocin by Fermentation Streptomyces sp. Y-84,36210 is cultured on yeast-/malt agar of the following composition:

| | |
|---|---|
| Malt extract | 10.0 g |
| Yeast extract | 4.0 g |
| Glucose | 4.0 g |
| Agar | 15.0 g |
| Distilled water | 1 l |
| pH | 7.0 |

The medium is distributed in test tubes and sterilized at 121° C. for 30 minutes. The test tubes are cooled in a slanting position to prepare agar slants. The agar slants are inoculated with the culture and incubated at 28° C. for 10 to 15 days, after which satisfactory growth and spore formation are observed. A suspension of the spores from one agar slant in distilled water is used to inoculate 5 500 ml Erlenmeyer flasks each containing 100 ml of the seed culture medium, or a 5 liter suction flask containing 1 liter of the same seed culture medium.

| Composition of the seed culture medium | |
|---|---|
| Glucose | 15.0 g |
| Soybean meal | 15.0 g |
| Corn steep liquor | 5.0 |
| $CaCO_3$ | 2.0 g |
| NaCl | 5.0 g |
| Distilled water | 1 l |
| pH | 6.5 |

The abovementioned medium is distributed in 100 ml portions in each 500 ml Erlenmeyer flask or in 1 liter portions in each 5 liter suction flask and is sterilized at 120° C. for 30 minutes. The flasks are cooled, inoculated with the spore suspension, and shaken at 27° C. (+1°C.) and 240 rpm in a rotary shaker with a 3.8 cm (1.5 inch) excursion for 72 hours. The product which has grown in this way is used to inoculate two 15 liter glass fermenters containing 10 liters of 8-10% by volume seed culture medium for the preparation of the 2nd stage of the seed culture. The fermentation is carried out at 27° C. (+1°C.), stirring at 180-200 rpm and with an aeration rate of 6-7 lpm for a period of 24 hours. The well-grown 2nd stage of the seed culture which is obtained in this way is used to inoculate the production medium.

| Composition of the production medium | |
|---|---|
| Glucose | 15.0 g |
| Soluble starch | 20.0 g |
| Soyatone | 3.0 g |
| Peptone | 3.0 g |
| $CaCO_3$ | 2.0 g |
| NaCl | 2.0 g |
| Corn steep liquor | 2.0 g |
| $(NH_4)_2SO_4$ | 0.5 g |
| Distilled water | 1 l |
| pH | 6.5 |

0.025% DESMOPHEN is added to the contents of the fermentor as antifoam agent.

280 liters of the above medium are placed in a 390 liter fermentation tank. The medium is sterilized at 121° C. by indirect or direct steam for 28 minutes. The fermentation tank is cooled and inoculated with the 2nd stage of the seed culture (7% by volume). The fermentation is carried out at 27° C. (+1°C.), stirring at 100-120 rpm. The aeration rate is 170 liters per minute. When the fermentation has terminated after 40-45 hours, the diameter of the zone of inhibition of Staphylococcus aureus 209 P is 20 mm when the culture filtrate is tested by the agar well method (6 mm diameter) using agar to which calcium is added (30 mM) at a pH of the culture liquid in the range 6.5 to 6.9.

The packed cell volume is 20%.

The harvested culture broth containing the antibiotic complex is centrifuged to separate the mycelium from the culture liquid and is further processed as described in Example 4.

EXAMPLE 3

Culturing of Streptomyces sp. Y-84,36210 for the Preparation of Cammunocin by Fermentation The process described in Example 2 is repeated under the following conditions:

Str. sp. Y-84,36210 is cultured on an agar medium having the following composition:

| | |
|---|---|
| Starch (soluble) | 10.0 g |
| $K_2HPO_4$ | 1.0 g |
| $MgSO_4.7H_2O$ | 1.0 g |
| NaCl | 1.0 g |
| $(NH_4)_2SO_4$ | 2.0 g |
| $CaCO_3$ | 2.0 g |
| $FeSO_4.7H_2O$ | 0.1 mg |
| $MoCl_2.4H_2O$ | 0.1 mg |
| $ZnSO_4.7H_2O$ | 0.1 mg |
| Agar | 15.0 g |
| Distilled water | 1 l |
| pH | 7.2 |

The composition of the seed culture medium is the same as that described in Example 2.

| | |
|---|---|
| Glucose | 20.0 g |
| Soybean meal | 10.0 g |
| $CaCO_3$ | 0.2 g |
| $CoCl_2.6H_2O$ | 1.0 mg |
| Distilled water | 1 l |
| pH | 7.0 |

100 liters of the above medium are placed in a 150 liter fermentation tank. The medium is sterilized at 121° C. by indirect or direct steam for 28 minutes. The fermentation tank is cooled and inoculated with the 2nd stage of the seed culture (9% by volume). The fermentation is carried out at 27° C. (+1°C.), stirring at 80-90 rpm with an aeration rate of 60-70 liters per minute. When the fermentation is terminated after 40-45 hours, the pH of the culture broth is 6.45 and the diameter of the zone of inhibition of *Staphylococcus aureus* 209 P is 22 mm when the culture filtrate is tested by the agar well method (6 mm diameter) using agar to which calcium is added (30 mM). The packed cell volume is 12% by volume. The culture broth is further processed as described in Example 5.

EXAMPLE 4

240 ml of the culture filtrate obtained as in Example 2 are loaded onto a column containing 6 liters of the anion exchange resin AMBERLITE IRA 68 ($Cl^-$) (exchange resin with polystyrene/polyamine functionality). After the column has been washed with 40 liters of demineralized water it is eluted with aqueous 2.0M NACl solution, pH 8.5 (adjusted with ammonia). The resulting active eluates (30 liters) are extracted 3 times with an ethyl acetate: n-propanol 2:1 mixture after the pH has been adjusted to 4.0 with HCl. The extracts are concentrated in vacuo, and the concentrate (6.1 g) obtained in this way is subjected to silica gel chromatography (particle size 0.062-0.037 mm (230-400 mesh, 600 g) and eluted with a gradient from chloroform to chloroform:methanol (1:1). The combined concentrated active fractions (3 g) are extracted with a saturated aqueous $NaHCO_3$ solution, and then the pH of the extract is adjusted to 4.0 with HCl, after which renewed extraction with an ethyl acetate:n-propanol 2:1 mixture is carried out. The extract is concentrated in vacuo, resulting in 1.8 g of the compound, which is then subjected to a silica gel chromatography (particle size 0.062-0.037 mm (230-400 mesh) 360 g). Elution is carried out with a gradient from ethyl acetate to ethyl acetate:methanol (1:1) and, on concentration, provides 860 mg of active material. This material is divided into 6 portions and separately loaded onto columns containing 50 g of SEPHADEX LH-20 (lipophilic gel filtration material) in methanol; methanol is used as eluent. 360 mg of cammunocin are obtained in this way.

EXAMPLE 5

The culture filtrates from the two fermenter batches in Example 3 are combined to result in a volume of 185 liters. This amount is loaded onto a column containing 4 liters of AMBERLITE IRA-68 ($Cl^-$); the column is washed with 20 liters of demineralized water and eluted with aqueous 2.0M sodium chloride solution which has been adjusted to pH 8.5 with ammonia. The resulting 47 liters of active eluates are loaded onto a column containing 3 liters of Diaion® HP-20 (polymeric adsorbent, from Mitsubishi Chemical Industries, Japan); the column is washed with 7 liters of demineralized water and eluted with methanol. The active methanol eluates are concentrated in vacuo, and the aqueous solution obtained in this way is diluted with distilled water. The pH is adjusted to 3.0 with HCl, and the solution is loaded onto a column containing 2 liters of DIAION HP-20. The column is washed with demineralized water until the wash-water is free of chloride ions. The cammunocin is eluted with methanol; the methanol eluates are concentrated in vacuo and freeze-dried. 21 g of the crude antibiotic complex are obtained in this way.

The crude antibiotic complex is dissolved in double-distilled water, pH 1.7 with ammonia, and the solution is divided into two equal volumes and loaded onto two columns which are 6.4×84 cm in size and contain SEPHADEX LH-20 in double-distilled water. The columns are eluted with double-distilled water at a flow rate of 0.5 ml per minute, and the eluate is collected in 20 ml fractions. In total, 1.1 liters of the active eluates are freeze-dried, resulting in 8 g of the antibiotic complex. This material is further purified by renewed chromatography on a column containing SEPHADEX LH-20 in the manner described above, resulting in 4.45 g of semi-pure antibiotic complex.

This semi-pure antibiotic complex is dissolved in 200 ml of double-distilled water and loaded onto a column (6.2×26 cm) containing DEAE-SEPHADEX A-25 (ion exchanger with diethylaminoethyl functionality) in double-distilled water. The column is washed with water and then eluted with an aqueous NACl solution, with its molarity being increased in a stepped gradient with 5% steps. The antibiotic complex is eluted in 6 liters of a 1.5M NACl solution and 5 liters of a 2M NACl solution. The combined eluates, whose pH has been adjusted to 2.0 with HCl, are then loaded onto a column containing 2 liters of DIAION HP-20; the column is washed with water until the wash-water no longer contains chloride ions and is then eluted with methanol. The methanol is removed by distillation in vacuo, and the remaining aqueous solution is freeze-dried, resulting in 700 mg of pure cammunocin.

EXAMPLE 6

HPLC of the pure antibiotic complex cammunocin on a column which is 4×120 mm in size and contains ODS-HYPERSIL (10 μ), using an eluent mixture composed of MEOH and 1% aqueous acetic acid (55:45), with a flow rate of 0.5 ml per minute and detection at 234 nm, shows that cammunocin is a microheterogeneous mixture, i.e. a complex of related antibiotic compounds, as is shown in FIG. 2.

Cammunocin is hydrolyzed with 6N HCl, and the hydrolyzate obtained in this way is, after methylation and trifluoroacetylation, analyzed by means of GC-EIMS (gas chromatography/electron impact mass spectrometry) and GC-CIMS (gas chromatography/mass spectroscopy with chemical ionization) using a Perkin Elmer gas chromatograph with 3% OV-1 on a Gaschromone Q column connected to an AEI MS-9025 mass spectrometer with a DS-50 SM on-line data system. This showed the presence of the following amino acids:

| Main constituents: | α-Aminoadipic acid |
| --- | --- |
| | Aspartic acid |
| | Glycine |
| | 4-Hydroxyphenylglycine |
| | Serine |
| Subsidiary constituents: | Glutamic acid |
| | 3-Hydroxyaspartic acid |
| | Leucine |
| | N-methylphenylglycine |
| | Proline |
| | Threonine |

The conclusion which may be drawn from the above data is that cammunocin is a peptide antibiotic complex.

Figure 4:
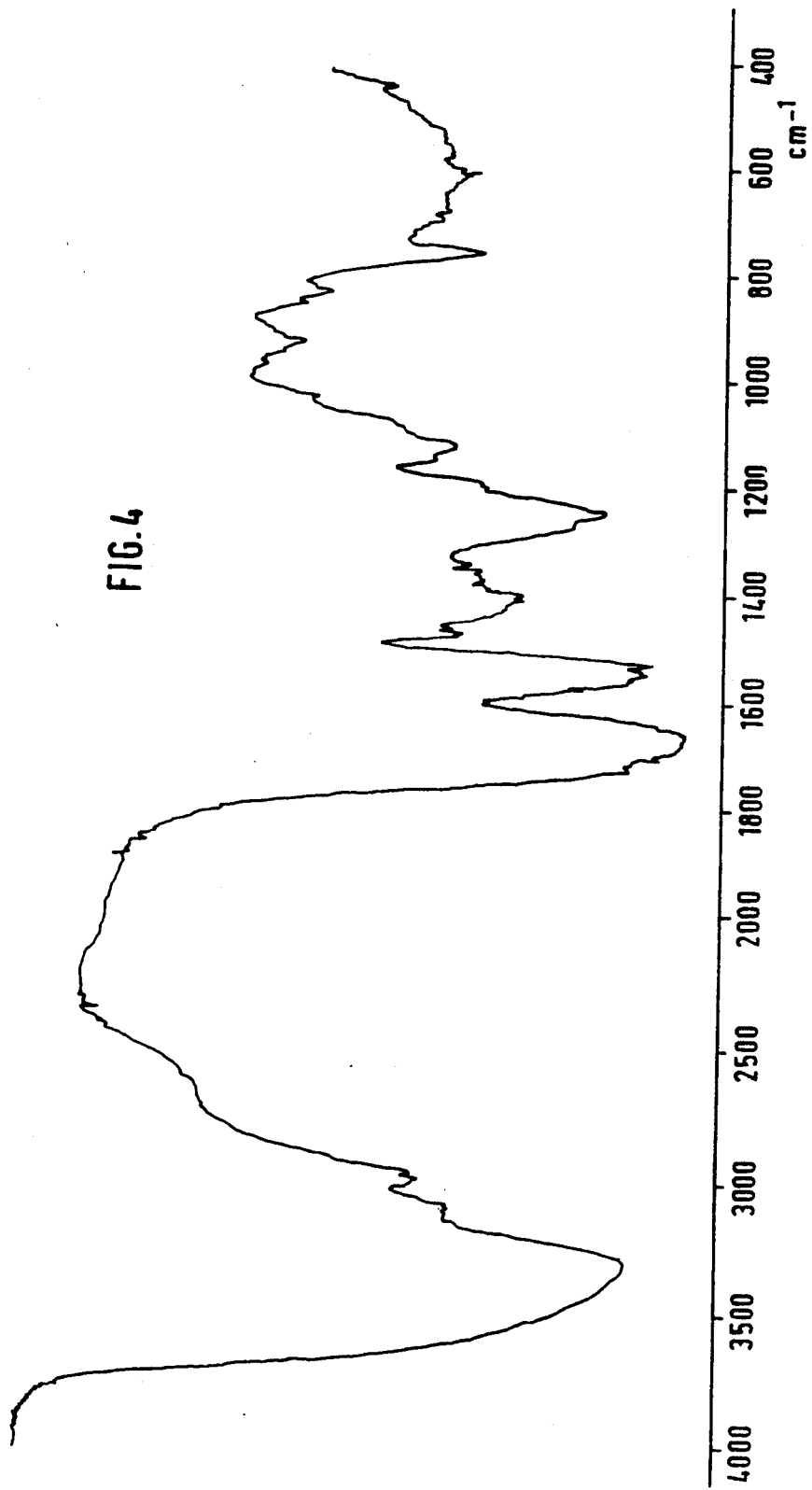
FIG. 4 shows the IR spectrum (KBr disk) recorded using a Perkin Elmer P. E. 521 spectrometer.

What is claimed is:

1. Purified, isolated cammunocin, substantially free of the microorganism Streptomyces species Y-84,36210, having the UV spectrum in methanol shown in FIG. 3, with bands at about 234 nm, 280 nm and 340 nm and the IR spectrum in KBr as shown in FIG. 4, with bands at about $3400 cm^{-1}$, $1680 cm^{-1}$, $1559 cm^{-1}$, $1250 cm^{-1}$, and $600 cm^{-1}$ and requiring the presence of calcium to exhibit an antibacterial effect against gram-positive bacteria.

2. Cammunocin as claimed in claim 1, obtained by cultivating Streptomyces species Y-84,36210 and subsequently isolating and purifying cammunocin.

3. A pharmaceutical composition which comprises cammunocin as claimed in claim 2, together with one or both of a pharmaceutically acceptable auxiliary and vehicle.

4. A pharmaceutical composition according to claim 3 having antibacterial activity against gram-positive bacteria in the presence of calcium.

5. A pharmaceutical composition according to claim 3 having immunosuppressant activity.

6. A pharmaceutical composition according to claim 3 having antibiotic activity.

* * * * *